United States Patent [19]

Lundberg

[11] 4,409,981

[45] Oct. 18, 1983

[54] MEDICAL ELECTRODE

[75] Inventor: Chris A. Lundberg, Woodbury, Minn.

[73] Assignee: Minnesota Mining and Manufacturing Company, St. Paul, Minn.

[21] Appl. No.: 285,254

[22] Filed: Jul. 20, 1981

[51] Int. Cl.³ .............................................. A61B 5/04
[52] U.S. Cl. .................................................... 128/640
[58] Field of Search ............................... 128/639–641, 128/644, 798, 802, 803

[56] References Cited

U.S. PATENT DOCUMENTS

| | | | |
|---|---|---|---|
| 3,518,984 | 7/1970 | Mason | 128/640 |
| 3,774,592 | 11/1973 | Lahr | 128/640 |
| 3,805,769 | 4/1974 | Sessions | 128/641 |
| 3,862,633 | 1/1975 | Allison et al. | 128/641 |
| 3,868,946 | 3/1975 | Hurley | 128/641 |
| 4,051,842 | 10/1977 | Hazel et al. | 128/640 |
| 4,067,322 | 1/1978 | Johnson | 128/641 |
| 4,102,331 | 7/1978 | Grayzel et al. | 128/640 |
| 4,126,126 | 11/1978 | Bare et al. | 128/639 |
| 4,353,372 | 10/1982 | Ayer | 128/640 |

OTHER PUBLICATIONS

EKG Stress Test Electrode Brochure, Cat. No. 370.

*Primary Examiner*—Lee S. Cohen
*Attorney, Agent, or Firm*—Donald M. Sell; James A. Smith; Robert W. Hoke, II

[57] ABSTRACT

A disposable medical electrode having a configuration wherein the various sheets forming the electrode have at least two common edges thereby affording the manufacture of the electrode by a method comprising the cutting and laminating together of various continuous webs, the location and placement of which can be controlled, in an automatable process.

4 Claims, 4 Drawing Figures

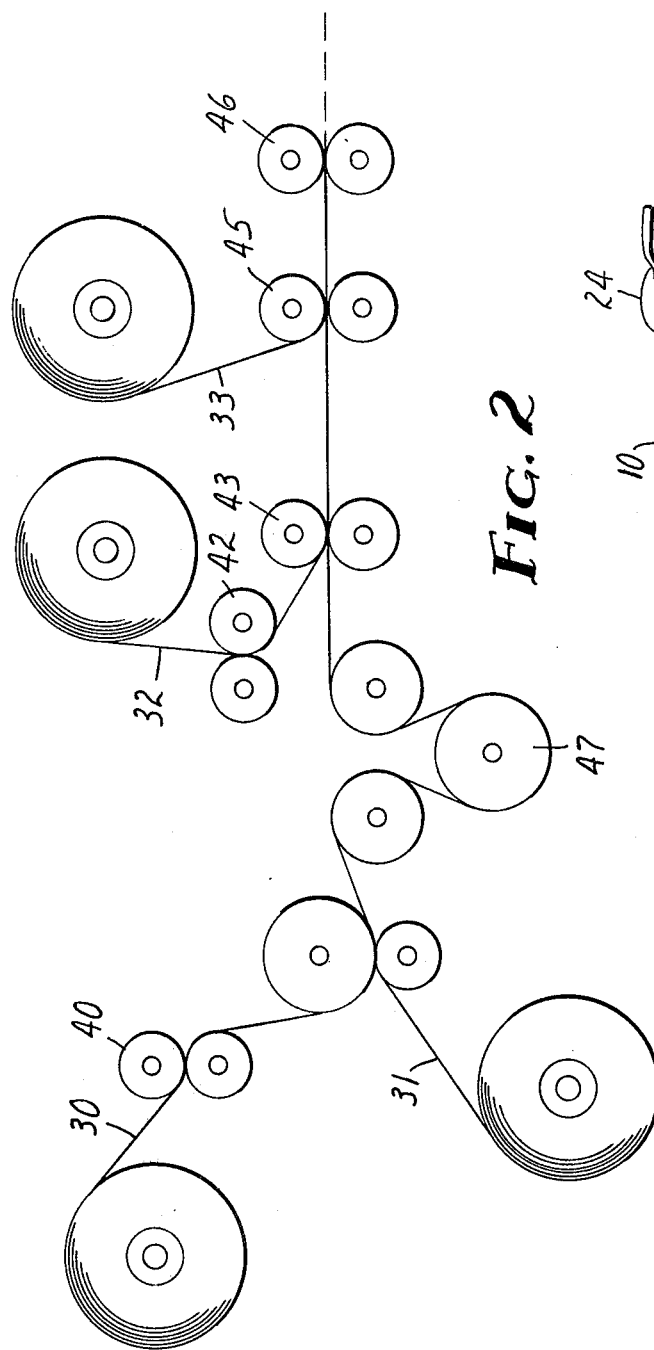
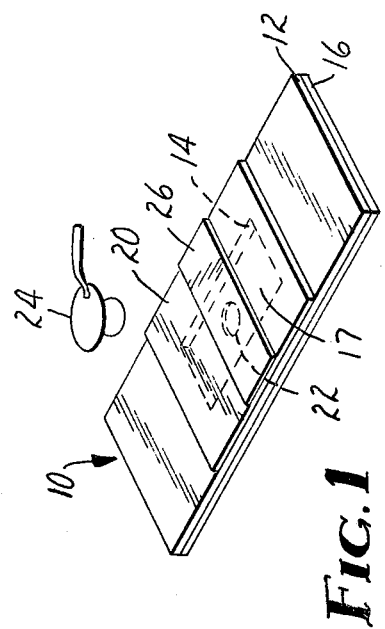

MEDICAL ELECTRODE

BACKGROUND OF THE INVENTION

This invention relates to disposable medical electrodes, and a method for making the same, and more particularly to disposable electrocardiogram electrodes.

The delivering or monitoring of electrical signals to or from the human body is widespread. Hence, many types of electrodes have been developed through which electrical contact with the human body can be made. These electrodes are either permanent (i.e., reusable) electrodes, or disposable electrodes which are utilized only for a single patient and then discarded. The disposable electrodes have largely resulted from attempts to reduce the costs involved in the upkeep and cleaning of the permanent electrode between uses, as well as the patient and electrode preparation required prior to each use of the permanent electrodes. Such cost reduction attempts, however, have necessarily been tempered to ensure that the integrity and quality of the electrical contact established by the electrode was not sacrificed. Hence, most of the existing disposable medical electrodes retain metallic (silver/silver chloride) portions embedded within a packaged conductive gel to achieve integrity within the electrical contact (See, e.g., U.S. Pat. No. 3,868,946). These metallic components make up a large portion of the electrode's cost and thus substantially limit the amount by which the manufacturing cost can be reduced. The requirement of accurately placing the metallic component within the electrode also severely limits the efficient automation of the electrode manufacturing process.

Another concern with the development of disposable electrodes was the potential that the conductive gel contained therein and used to increase the electrical contact between the electrode and the human body, might eventually desiccate, or might otherwise migrate to undesirable locations on the electrode, prior to the use of the electrode, thus conceivably degrading, if not destroying, the electrode's efficacy. To prevent either of these occurrences the existing electrodes generally incorporated an integral and centralized cup-like cavity in which the conductive gel was restrained and sealed (See e.g. U.S. Pat. No. 4,126,126), and which had an adhesive coated flange-like projection extending outward from the side of the cavity to attach the electrode to the human body. To facilitate the manufacture of this central cavity and projecting flange, the existing electrodes typically had the configuration of a disk with all of the electrodes's components centrally mounted thereon. This configuration, although allowing a partially automated manufacturing process, still required substantial manual interface to critically align the various components forming the electrode.

SUMMARY OF THE INVENTION

The disposable medical electrode according to the present invention has a configuration permitting its manufacturing process to be automated, thereby affording a substantially less expensive disposable electrode. This method comprises cutting an opening at each of a plurality of predetermined locations spaced longitudinally along a first web of an adhesive coated material. A release liner web is laminated to the adhesive coated surface of this first web, with the release liner web covering the openings and with the periphery of each of the openings and the release liner thereon creating a plurality of reservoirs therein. A conductive gel is introduced into each of those reservoirs by any of a variety of methods. The reservoirs are then covered by laminating a second web to the surface of the first web opposite the release liner, with the second web covering and extending beyond each of the openings in the first web. Prior to this lamination, a plurality of holes are cut into the second web at predetermined locations spaced longitudinally along this second web and corresponding to the spacing of the openings in the first web. When the second web is positioned on the first web, these holes are essentially centrally positioned over the openings in the first web. A third web is then laminated to the surface of the second web opposite the first web, with the third web covering and extending beyond each of the holes in the second web. This laminate (i.e., release liner, first, second, and third web) is then cut at predetermined intervals spaced longitudinally along the laminate, thereby separating the laminate into a plurality of individual electrodes, Since the configuration of the electrodes according to the present invention facilitates their direct manufacture from a plurality of laminated and continuous webs, greater control can be achieved over the placement of each of the components forming the electrodes. This control makes is possible to accurately position the various components at higher manufacturing speeds and with a substantially reduced labor requirement. The resulting rectangular configuration also lends itself to narrower electrodes having at least one straight edge, both of which facilitate the placement of the finished electrode upon the patient.

DESCRIPTION OF THE DRAWING

The present invention will be further described hereinafter with reference to the accompanying drawing wherein:

FIG. 1 is a perspective view of a single electrode according to the present invention, FIG. 2 is a schematic representation of a method of manufacturing medical electrodes according to the present invention;

DETAILED DESCRIPTION OF THE PREFERRED EMBODIMENT

Figure 3:
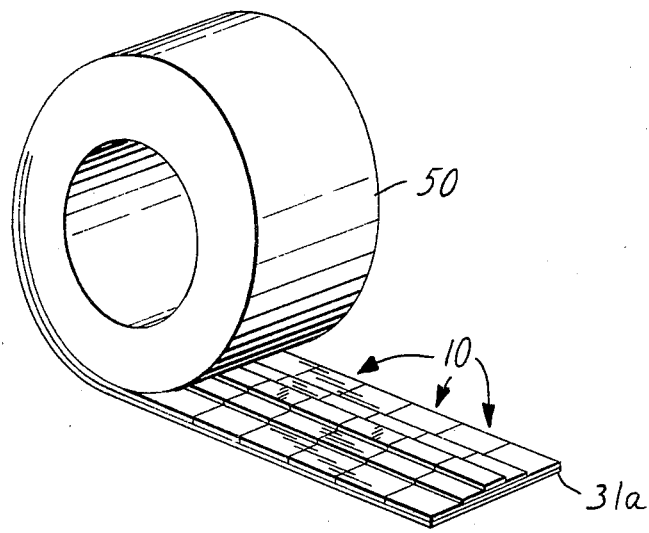
FIG. 3 is a perspective view of a plurality of electrodes on a roll of release liner according to the present invention.

A disposable electrode 10 according to the present invention is best illustrated in FIG. 1. This electrode 10 has been die cut from a plurality of laminated elongate webs 30, 32, and 33 (see FIG. 2), thus facilitating a simplified manufacturing process and a lower cost for the electrodes 10 manufactured. Each of the electrodes 10 comprises a first sheet 12, typically a flexible foam material having one surface which is coated with a suitable adhesive. The flexibility of this foam permits its conformance to the varied configuration of the human body. The first sheet 12 has a rectangular opening 14 which has been die cut therethrough and which is spaced from each of the edges forming the outer boundaries of the first sheet. Other shaped openings are, of course, also viable. A removable release liner 16, typically a silicone coated paper, is laminated to the first sheet 12. This lamination can occur after the opening 14 has been cut, or alternatively prior to die cutting the opening providing adequate control can be achieved over the depth of the die cutting operation to ensure that the release liner 16 is left intact sealing one end of the opening 14. A reservoir 17 is thus created within the electrode 10, bordered by the release liner 16 and the periphery of the opening 14. An electrically conductive gel is dispensed or introduced into this reservoir 17 and the portion of the opening 14 remaining uncovered is sealed to retain the gel within the reservoir 17 and to prevent the gel from desiccating. The sealing of the opening 14 is done with a relatively stiff but yet resilient second sheet 20, such as a sheet of polyester, commercially available from Eastman Kodak of New York, which is laminated over the opening 14 to the surface of the first sheet 12 opposite the release liner 16. The second sheet 20 of the preferred embodiment is also adhesive coated facilitating its attachment to the first sheet 12. The second sheet 20 is slightly larger in width than the opening 14 and therefore will extend beyond the boundaries of the opening 14 permitting the adhesive on the second sheet 20 to affix the second sheet 20 to the first sheet 12, and thereby seal the reservoir 17. The second sheet 20 has a hole 22 die cut therethrough which is disposed within the second sheet 20 so that it will be essentially centrally positioned over the opening 14 when the second sheet 20 is laminated to the first sheet 12. This hole 22 is adapted to receive a connecting lead 24 from certain electrical equipment (not shown) to which the electrode 10 is to be connected. In order to secure the lead 24 within the reservoir 17, the hole 22 is slightly smaller than the portion of the lead 24 which must be received. Thus, the second sheet 20 must be adequately resilient to permit the entrance and retention of the lead 24. The second sheet 20 must also be relatively stiff to provide a supported surface on the foam through which the lead 24 can be inserted. A third sheet 26, typically a flexible vinyl material, is affixed over the hole 22, to the surface of the second sheet 20 opposite the first sheet 12. This third sheet is adhesively coated on one surface and has a width slightly greater than the hole 22 so that it extends beyond the boundaries of the hole 22 and may therefore be affixed to the second sheet 20, sealing the hole 22. This third sheet 26 can be designed to be removable prior to the insertion of the lead 24 or it can be designed to be punctured by the lead 24 when the lead 24 is inserted in the hole 22. It is important to note that due to the manufacturing method for these electrodes 10, the first, second, and third sheets (12, 20 and 26 respectively) forming the electrode 10 have at least two edges in common. This limitation exists because the sheets forming the individual electrodes are simultaneously die cut from elongate webs (30, 31, 32, and 33) which have been laminated together during the manufacture of the electrode. This final die cutting operation, separating the lamination into individual electrodes, cuts the webs along two or more defined lines which become the common edges of the various sheets forming the electrode. This final die cutting operation also creates the overall configuration of the electrode which in the case of the preferred embodiment is rectangular although other configurations are possible. The advantages of this structural limitation, i.e., that the sheets have two or more common edges, will become more apparent through the discussion of a method according to the present invention by which the electrodes 10 are manufactured.

Figure 4:
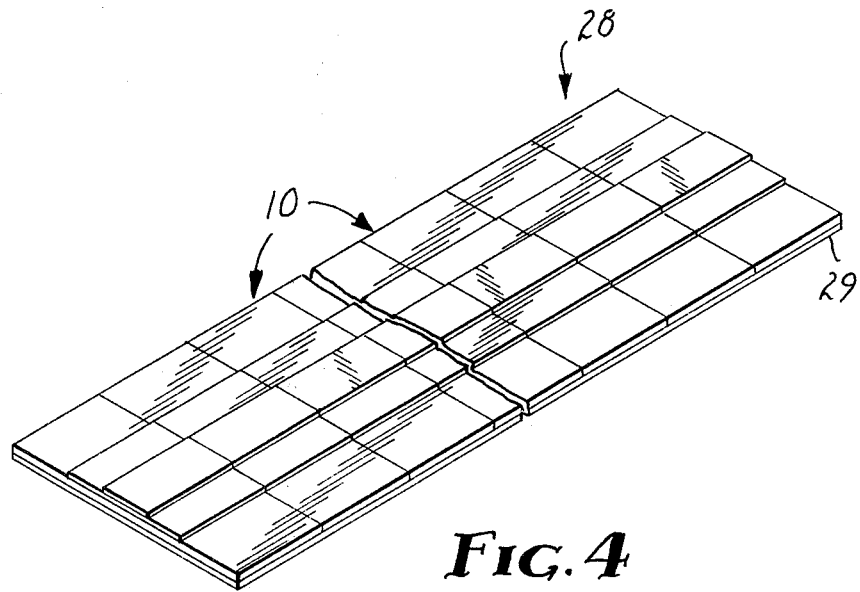
FIG. 4 is a perspective view of a plurality of electrodes on a strip of release liner according to the present invention.

FIG. 2 illustrates in schematic form the preferred embodiment of the method according to the present invention, for manufacturing the medical electrodes 10. This method comprises a first die cutting operation in which a conventional die-cutting press and associated dies 40 cut a plurality of openings 14 at predetermined locations spaced longitudinally along a first web 30, i.e., the adhesive coated foam material. A release liner web 31 is then laminated to the first web 30 by conventional lamination means 41. This lamination defines the reservoir 17 into which the conductive gel is introduced. Depending upon the exact physical properties of the conductive gel 18, a roll coater 47, or some other technique of introducing this gel is utilized. A second web 32 is then laminated by conventional lamination means 43 to the surface of the first web 30 opposite the release liner 31. A plurality of holes 22 with a longitudinal spacing facilitating the alignment of the holes 22 over the openings 14 in the first web 31, are cut by a conventional press and associated dies 42 into the second web 32 prior to this lamination. The holes 22 are then covered by the lamination of a third web 33 to the second web 32. This is also done by conventional laminating means 45. It is extremely important to note that at this stage of the manufacturing method, all components making up the lamination are in web form. Since both ends of each of the webs are controlled, the various components can be oriented with respect to each other with an accuracy and at a speed not otherwise possible when the electrode consists of individual components which are individually assembled. This retention of control over the individual components making up the electrode 10 contributes to a reduction in the manufacturing cost of the electrode 10. Thus, only after all of the components have been aligned with respect to each other and laminated together, are the individual electrodes die cut from that lamination. This final die cutting operation utilizes a conventional press and associated dies 46 which are similar to those used in the previous die cutting operations. It is possible, however, by controlling the depth within the lamination in which this final die cutting occurs, to selectively leave the release liner web 31 intact (i.e., cutting only the first, 30, second, 32, and third 33 webs with the dies 46). This affords a number of alternative embodiments for the electrode 10. For instance, FIG. 1 illustrates the results of a final die cutting operation the entire lamination including the release liner web 31 is cut during each and every cycle; i.e., this method produces individual electrodes 10 which are not connected to each other. As an alternative to this, FIG. 3 illustrates the results of a final die cutting operation where only the first, second, and third webs 30, 32, and 33 respectively, are die cut and the release liner web 31 is left intact. In this case, a plurality of adjacent electrodes 10 are produced which are adhesively attached to a continuous release liner web 31a. This provides a plurality of electrodes which can be wound into a convoluted roll 50, to be used with dispensing apparatus similar to the conventional label dispensers, to dispense individual electrodes. This format allows individual electrodes to be dispensed from a master roll only as they are needed by the consumer. A third alternative is illustrated in FIG. 4 wherein is shown an electrode strip 28 comprising a predetermined number of electrodes 10 adhesively attached to a release liner strip 29. This configuration occurs when the entire lamination including the release liner web 31 is cut at selected intervals corresponding to the length of the release liner strip 29, while between these selected intervals only the first, second, and third webs, 30, 32, and 33 respectively, are die cut separating the electrodes 10 but leaving the release liner web 31 intact. Typically, this embodiment has ten electrodes adhesively attached to a release liner strip 29. This number of electrodes is convenient because it corresponds to the number of electrodes typically required for an electrocardiogram. As a variation of this embodiment, it is also possible to laminate the third web 33 after the first and second webs, 30 and 32 respectively have been die cut. The third web 33 is then left intact over the entire strip of electrodes. Since in this embodiment all the electrodes on the strip will be used at the same time, the third web 33 can be removed by the user prior to applying the various electrodes.

Having thus described some preferred embodiments of the present invention it must be understood that changes may be made in the size, shape, or configurations of some of the elements described herein without departing from the present invention as recited in the appended claims.

What is claimed is:

1. A disposable medical electrode for connecting electrical equipment to the skin of a patient, which electrode has been cut from a plurality of elongate webs, said electrode comprising a first sheet comprising a first surface adapted to adhere to the skin of a patient, a second surface and at least two edges connecting the first surface to the second surface, said first sheet having an opening therethrough which is spaced from each of the edges of said first sheet, a removable release liner sheet laminated to said first surface of said first sheet and covering said opening, said release liner and the perphery of said opening defining a reservoir within the electrode, a relatively stiff but yet resilient second sheet comprising (1) a first surface affixed to the second surface of said first sheet opposite said release liner, (2) a second surface and (3) at least two edges connecting the first surface to the second surface and in common with said edges of said first sheet, said second sheet covering said opening, and having a hole therethrough adapted to receive a connecting lead for the electrical equipment, said hole being positioned adjacent said opening, a conductive gel within said reservoir, and a third sheet comprising (1) a first surface affixed to the second surface of said second sheet opposite said first sheet, (2) a second surface and (3) at least two edges connecting the first surface to the second surface and in common with said edges of said first and second sheets, said third sheet covering said hole.

2. A disposable electrode as claimed in claim 1 wherein said third sheet is releasably affixed to said second sheet to permit the removal, thereby affording access to said hole for the insertion of the connecting lead into said reservoir.

3. A disposable electrode as claimed in claim 1 wherein said third sheet remains affixed to said second sheet and wherein said third sheet is a puncturable material affording the piercing of said third sheet through the application of external force on the connecting lead, and the insertion of the connecting lead into said reservoir through the puncture above said hole.

4. An electrode strip comprising a release liner strip and a predetermined number of electrodes adhesively attached to said release liner strip, each of said electrodes comprising a first rectangular sheet having opposing surfaces, one of which is adapted to adhere to the skin of the patient and which is not adhering to said release liner strip, said first sheet having an internal opening between said surfaces, a stiff resilient second rectangular sheet affixed to said surface of said first sheet opposite said release liner, covering said opening, said second sheet having a hole therethrough which is smaller in area than said opening, said hole being essentially centrally positioned with respect to said opening, said release liner, said second sheet, and the periphery of said opening defining a reservoir within the electrode, said second sheet and said first sheet having at least two common edges resulting from the method of manufacture, a conductive gel within said reservoir, and a third rectangular sheet affixed to said second sheet, on the surface opposite said first sheet, covering said hole, said third sheet having at least two common edges with said first and second sheets.

* * * * *